(12) United States Patent
Kuduva et al.

(10) Patent No.: US 10,457,695 B2
(45) Date of Patent: Oct. 29, 2019

(54) PROCESS FOR THE PREPARATION OF TAVABOROLE

(71) Applicant: Glenmark Life Sciences Limited, Solapur (IN)

(72) Inventors: Srinivasan Subramanian Kuduva, Navi Mumbai (IN); Rajender, Telangana (IN); Mahendra Joma Choraghe, Navi Mumbai (IN); Samir Naik, Thane (IN); Shekhar Bhaskar Bhirud, Mumbai (IN)

(73) Assignee: Glenmark Life Sciences Limited, Solapur (IN)

( * ) Notice: Subject to any disclaimer, the term of this patent is extended or adjusted under 35 U.S.C. 154(b) by 0 days.

(21) Appl. No.: 16/070,002

(22) PCT Filed: Jan. 12, 2017

(86) PCT No.: PCT/IB2017/050145
§ 371 (c)(1),
(2) Date: Jul. 13, 2018

(87) PCT Pub. No.: WO2017/125835
PCT Pub. Date: Jul. 27, 2017

(65) Prior Publication Data
US 2019/0023724 A1    Jan. 24, 2019

(30) Foreign Application Priority Data
Jan. 18, 2016   (IN) .............................. 201621001791

(51) Int. Cl.
*C07F 5/02* (2006.01)
*A61K 31/00* (2006.01)

(52) U.S. Cl.
CPC .............. *C07F 5/025* (2013.01); *A61K 31/00* (2013.01)

(58) Field of Classification Search
CPC ................................ C07F 5/025; A61K 31/00
See application file for complete search history.

(56) References Cited

U.S. PATENT DOCUMENTS

2014/0349853 A1   11/2014   Maclean et al.

FOREIGN PATENT DOCUMENTS

| WO | 2014197634 A2 | 12/2014 |
| WO | 2015171186 A1 | 11/2015 |

OTHER PUBLICATIONS

Gunasekera et al. ("Practical synthesis and applications of benzoboroxoles", Tetrahedron, vol. 63, Issue 38, Sep. 2007, pp. 9401-9405).*

* cited by examiner

*Primary Examiner* — Rosalynd A Keys
(74) *Attorney, Agent, or Firm* — Ryan, Mason & Lewis, LLP

(57) ABSTRACT

The present invention relates to process for preparation of tavaborole with high purity. The present invention relates to method of assessing the purity of tavaborole.

11 Claims, 3 Drawing Sheets

PROCESS FOR THE PREPARATION OF TAVABOROLE

PRIORITY

This application claims priority under 35 U.S.C. § 371 to International Application No. PCT/IB2017/050145, filed Jan. 12, 2017 which claims the benefit of IN201621001791 filed Jan. 18, 2016, and entitled "PROCESS FOR THE PREPARATION OF TAVABOROLE", the contents of which are incorporated herein by reference.

FIELD OF THE INVENTION

The present invention relates to a process for the preparation of tavaborole and salts thereof.

BACKGROUND OF THE INVENTION

Tavaborole is an oxaborole antifungal indicated for the topical treatment of onychomycosis of the toenails due to *Trichophyton rubrum* or *Trichophyton mentagrophytes*. Tavaborole, chemically known as 5 fluoro-1,3-dihydro-1-hydroxy-2,1-benzoxaborole, is represented by compound of formula I,

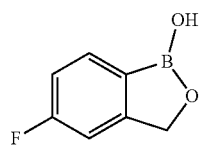

Tavaborole is currently marketed in United States under the trade name KERYDIN™ topical solution, 5% contains tavaborole, 5% (w/w) in a clear, colorless alcohol-based solution for topical use. Tavaborole is a white to off-white powder.

In one embodiment, the present invention provides a novel process for the preparation of tavaborole which provides a better purity profile and which can be easily performed on industrial scale.

SUMMARY OF THE INVENTION

The present invention provides a process for the preparation of tavaborole, a compound of formula I, comprising:

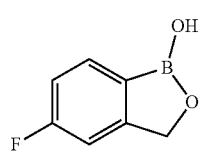

a) reacting 2-halo-5-fluorotoluene, a compound of formula II

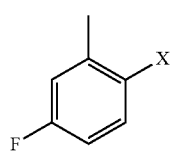

with a borate ester to obtain 2-methyl-4-fluorophenylboronic acid, a compound of formula III, wherein X is a halogen selected from chloro, bromo or iodo;

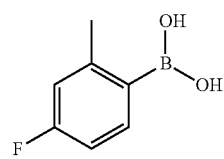

b) converting the compound of formula III to 2-halomethyl-4-fluorophenylboronic acid, a compound of formula IV

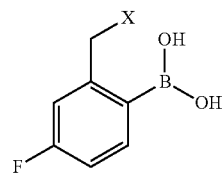

in the presence of mixture of halogenating agents; and c) cyclizing the compound of formula IV to obtain tavaborole.

In one embodiment, the present invention provides a process for the preparation of tavaborole comprising isolating tavaborole from a mixture of water and an organic solvent selected from $C_{1-4}$ alcohols, ethers, amides, esters, nitriles, sulfoxides, ketones, hydrocarbons and halogenated hydrocarbons or mixtures thereof.

In one embodiment, the present invention provides tavaborole, the compound of formula I

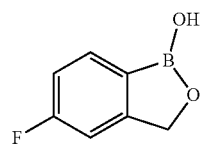

wherein the level of the compound of formula V and/or the level of compound of formula XIV, is less than 0.5% w/w as determined by HPLC.

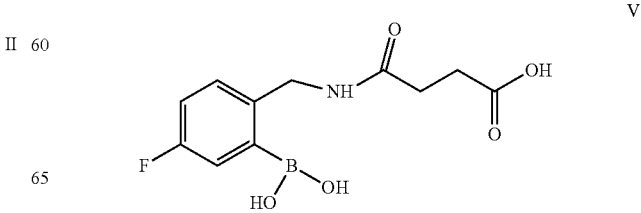

-continued

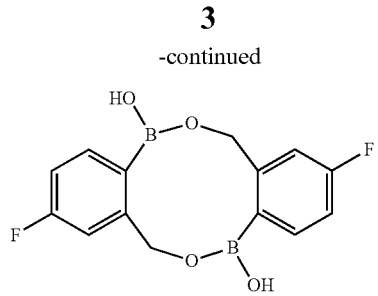

XIV

In one embodiment, the present invention provides a method for preparing tavaborole, comprising the steps of:
(a) providing a batch of tavaborole or a salt thereof;
(b) assessing the purity of said batch of tavaborole, by using the compound of formula V or the compound of formula XIV as a reference marker to determine the level of compound of formula V or the compound of formula XIV; and
(c) selecting the batch of tavaborole only if the % of the compound of formula V or the compound of formula XIV is less than 0.15% w/w as determined by HPLC.

In one embodiment, the present invention provides a method for preparing tavaborole, comprising the steps of:
(a) providing a standard solution of compound of formula V and/or the compound of formula XIV; and
(b) using the solution as a reference marker to determine the level of the compound of formula V or the compound of formula XIV.

DETAILED DESCRIPTION OF THE INVENTION

Figure 1:
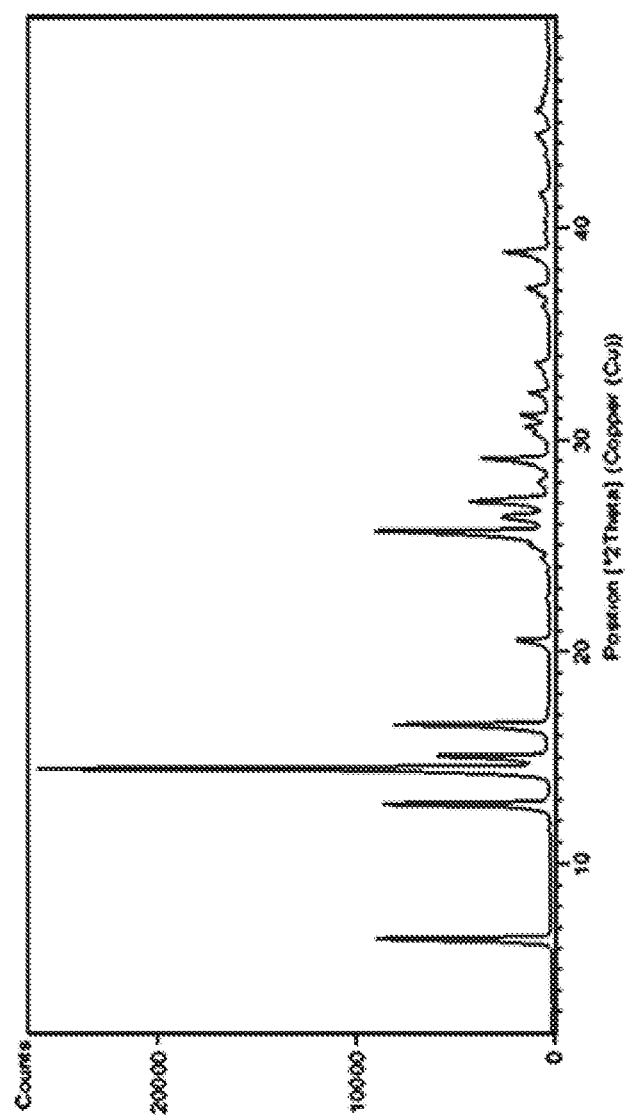
FIG. 1: XRD pattern of tavaborole according to example 7.
Figure 2:
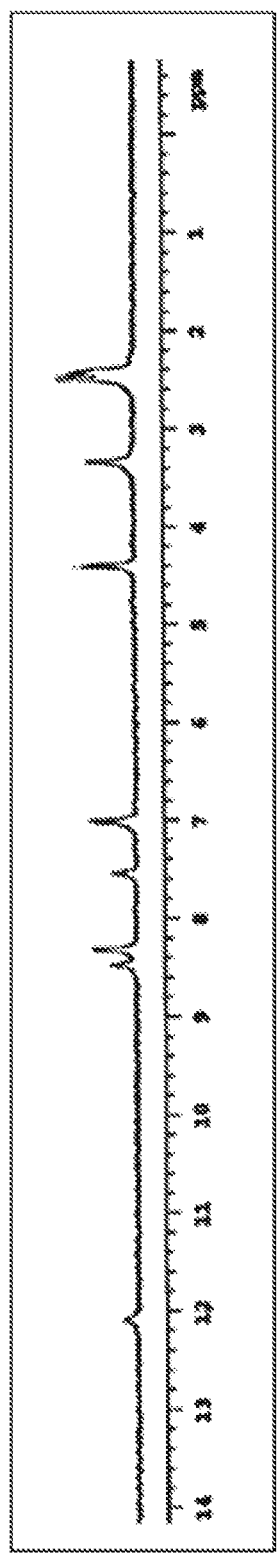
FIG. 2: NMR of compound of formula V according to example 8.
Figure 3:
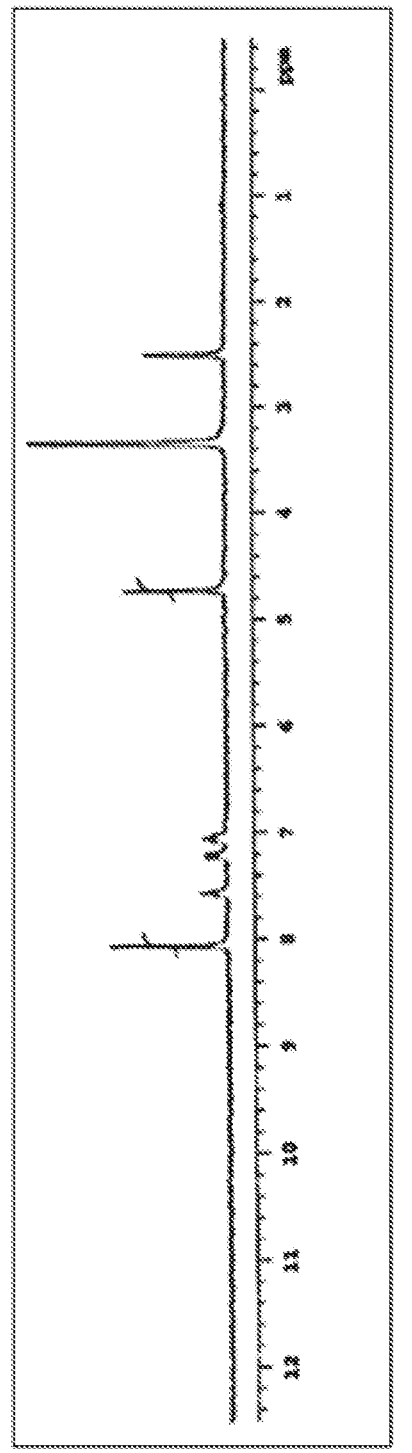
FIG. 3: NMR of compound of formula XIV according to example 9.

The present invention provides a process for the preparation of tavaborole, a compound of formula I, comprising:

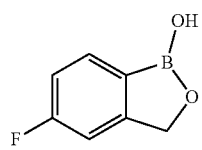

I a) reacting 2-halo-5-fluorotoluene, a compound of formula II

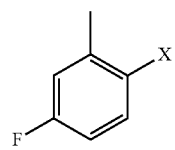

II with a borate ester to obtain 2-methyl-4-fluorophenylboronic acid, a compound of formula III, wherein X is selected from chloro, bromo or iodo;

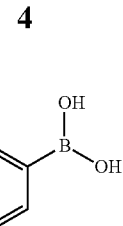

III b) converting the compound of formula III to 2-halomethyl-4-fluorophenylboronic acid, a compound of formula IV

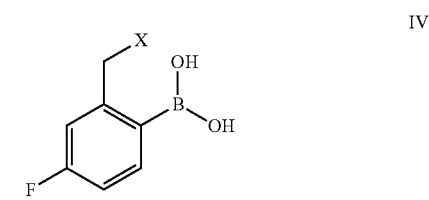 [SMILES: OB(O)c1ccc(F)cc1CBr]

IV in the presence of mixture of halogenating agents; and
c) cyclizing the compound of formula IV to obtain tavaborole.

In one embodiment, step a) of the above process involves reacting 2-halo-5-fluorotoluene with a borate ester in presence of a magnesium or lithium compounds to obtain 2-methyl-4-fluorophenylboronic acid.

The reaction may be carried out over a period of about 30 min to about 3 hours.

The reaction may be carried out in the presence of a suitable solvent.

The solvent may be selected from the group consisting of ethers such as diethyl ether, methyl tert butyl ether, tetrahydrofuran, 1,4-dioxane, tetrahydropyran and the like; hydrocarbons such as toluene, cyclohexane, heptane, hexane, xylene and the like; halogenated solvents such as methylene dichloride, ethylene dichloride, chloroform, carbon tetrachloride and the like.

The borate ester may be selected from the group consisting of triisopropyl borate, trimethoxy borane, tributyl borate, triethyl borate and the like.

The lithium reagents may be selected from alkyl or cyclic compounds selected from the group consisting of n-butyllithium, isopropyllithium, methyllithium, sec-butyllithium, phenyllithium and cyclohexanyllithium.

In one embodiment, in step a) of the above process X is bromo.

In one embodiment, in step a) of the above process the compound of formula IIa, 2-bromo-5-fluorotoluene, is reacted with triisopropyl borate in tetrahydrofuran in presence of butyl lithium to obtain the compound of formula III.

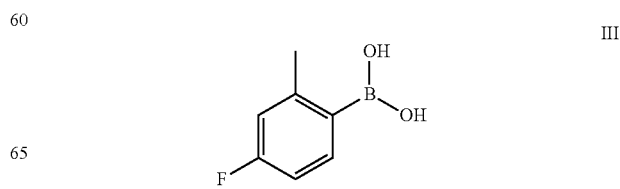

III

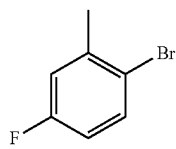

IIa

In one embodiment, step b) of the above process involves converting the compound of formula III to 2-halomethyl-4-fluorophenylboronic acid, a compound of formula IV in the presence of mixture of halogenating agents.

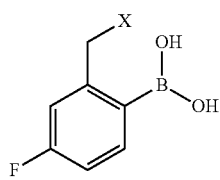

IV

In one embodiment, the halogenating agents may be selected from the group consisting of chlorinating agents, brominating agents or iodinating agents.

In one embodiment, the halogenating agents may be a mixture of chlorinating agents.

In one embodiment, the halogenating agents may be a mixture of brominating agents.

In one embodiment, the halogenating agents may be a mixture of iodinating agents.

In one embodiment chlorinating agents may be selected from the group consisting of chlorine, N-chlorosuccinimide, N-chlorophthalimide, cyanuric chloride, trichloroisocyanuric acid, tert-butyl hypochlorite and the like; the brominating agents may be selected from the group consisting of bromine, N-bromosuccinimide, N-bromophthalimide, 1,3-dibromo-5,5-dimethylhydantoin, trimethyl-ammonium perbromide, thionyl bromide, phosphorous tribromide, phosphorous pentabromide, N-bromoacetamide, dibromoisocyanuric acid, or N-bromosaccharin and the like; the iodinating agent may be selected from the group consisting of Iodine, N-iodosuccinimide, N-iodosaccharin, 1,3-diiodo-5,5-dimethylhydantoin and the like.

In one embodiment, in step b) the compound of formula III is converted to the compound of formula IV using a mixture of halogenating agents in presence of radical initiator.

In one embodiment, step b) of the above process the mixture of halogenating agent is a mixture of brominating agent.

The radical initiator may be selected from the group consisting of azobisisobutyronitrile (AIBN) benzoyl peroxide, peracetic acid, 1,1'-azobis(cyclohexanecarbonitrile), 4,4-azobis(4-cyanovaleric acid), tert-butyl peroxybenzoate, potassium persulfate and the like.

In one embodiment, the radical initiator is azobisisobutyronitrile (AIBN).

In one embodiment, in step b) when X is bromo the above process involves converting the compound of formula III to 2-bromomethyl-4-fluorophenylboronic acid, a compound of formula IVa in the presence of mixture of brominating agents.

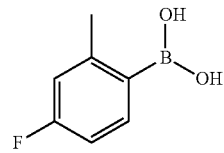

III

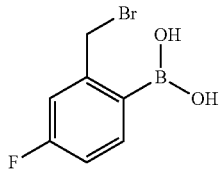

IVa

In one embodiment, the compound of formula III is converted to the compound of formula IVa by reacting with a mixture of brominating agents wherein the mixture of brominating agents comprises bromine and N-bromosuccinimide.

In one embodiment, the compound of formula III is converted to the compound of formula IVa using equimolar quantities of the brominating agents such as bromine and N-bromosuccinimide.

In one embodiment, bromine is used in catalytic amount with respect to the amount of N-bromosuccinimide used in conversion of the compound of formula III to the compound of formula IVa.

In one embodiment, N-bromosuccinimide is used in catalytic amount with respect to the amount of bromine used in conversion of compound of formula III to the compound of formula IVa.

In one embodiment, the compound of formula III is converted to the compound of formula IVa by reacting with a mixture of bromine and N-bromosuccinimide wherein bromine is used in catalytic amount with respect to the amount of N-bromosuccinimide.

It was surprisingly noted that in step b) involving conversion of the compound of formula III to compound of formula IVa, in the present invention, the reaction proceeded to completion at a faster rate when carried out using a mixture of brominating agents.

In one embodiment, in step b) the compound of formula III is converted to the compound of formula IVa using a mixture of brominating agents in presence of radical initiator.

In one embodiment, in step b) the compound of formula III is converted to the compound of formula IVa using a mixture of brominating agents in presence of azobisisobutyronitrile (AIBN).

In one embodiment, the conversion of the compound of formula III to the compound of formula IVa is carried out using a mixture of brominating agents in a suitable solvent.

The solvent may be selected from the group consisting of water, esters such as ethyl acetate, propyl acetate, butyl acetate, isopropyl acetate and the like; hydrocarbons such as heptane, hexane, toluene, xylene, n-heptane, cyclohexane and the like; halogenated solvents such as methylene dichloride, ethylene dichloride, chloroform, carbon tetrachloride, chlorobenzene and the like; ethers such as diethyl ether, methyl tert-butyl ether and the like; water, ketones such as acetone, methyl ethyl ketone, methyl isobutyl ketone and the like; sulpholanes; or mixtures thereof.

In one embodiment, in step b) involving bromination of the compound of formula III to obtain the compound of formula IVa, in the present invention, the reaction proceeded to completion at a faster rate when carried out using a mixture of brominating agents in methylene dichloride.

In one embodiment, the compound of formula III is converted to the compound of formula IVa using azobisisobutyronitrile (AIBN), N-bromosuccinimide and a catalytic amount of bromine in methylene dichloride.

In one embodiment, the reaction transpires over a temperature of about 0° C. to about reflux temperature of the solvent.

In one embodiment, the reaction transpires at reflux temperature of the solvent.

In one embodiment, the compound of formula III is converted to the compound of formula IVa in methylene dichloride by reacting with a mixture of bromine and N-bromosuccinimide.

In one embodiment, the reaction mixture comprising compound of formula IVa is subjected to treatment with water to remove any impurities.

In one embodiment, the compound of formula IV, obtained after halogenation is further treated with a base. The base may be selected from he group consisting of hydroxide such as sodium hydroxide, potassium hydroxide and the like; carbonates such as sodium carbonate, potassium carbonate and the like.

In one embodiment, when X is bromo, the reaction mass comprising compound of formula IVa is treated with a solution of a base. The process comprises adding the reaction mixture to the solution of base or adding the solution of base to the reaction mixture.

In one embodiment, the present invention provides a process for preparation of tavaborole, wherein the elimination of most, if not all, of the impurity of compound of formula V or the compound of formula XIV is achieved.

In one embodiment, the present invention provides a compound of formula V.

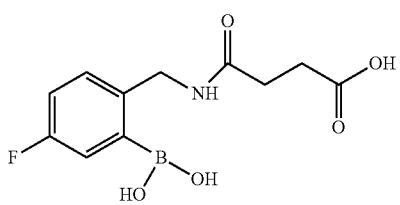

In one embodiment, the present invention provides a compound of formula V characterized by 1H NMR (DMSO) peaks at δ 2.414-2.497, 3.335, 4.387-4.408 6.999-7.030, 7.540, 8.315, 8.470, 12.094.

In one embodiment, the present invention provides a process for preparation of tavaborole, wherein the level of compound of formula V is less than 0.1% w/w as determined by HPLC, comprising subjecting the reaction mixture to treatment with water. The compound of formula V is a significant undesired by-product produced during the conversion of compound of formula III to tavaborole.

In one embodiment, the present invention provides a process for the preparation of tavaborole with high purity by subjecting the reaction mass comprising the compound of formula IV or the compound of formula IVa to treatment with water.

In one embodiment, the present invention provides a compound of formula XIV.

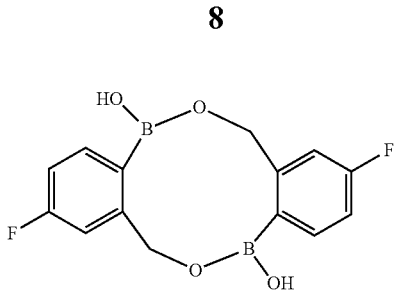

In one embodiment, the present invention provides a compound of formula XIV characterised by 1H NMR peaks at δ 2.502, 3.337, 4.728, 7.061-7.088, 7.200-7.230, 7.547-7.595, 8.059.

In one embodiment, the present invention provides a process for preparation of tavaborole, wherein the level of compound of formula XIV is less than 1% w/w as determined by HPLC, when the reaction mass comprising the compound of formula IVa was added to a solution of a base.

In one embodiment, in step c) of the present invention, the compound of formula IV is cyclized under acidic conditions.

In one embodiment, in step c) of the present invention when X is bromo, the aqueous layer comprising the compound of formula IVa, after basification was cyclized by treatment with a suitable acid.

The acid for cyclisation may be selected from the group consisting of mineral acids such as hydrochloric acid, sulfuric acid and the like; or organic acid such as acetic acid, trifluoroacetic acid and the like to obtain tavaborole, the compound of formula I.

In one embodiment, the compound of formula IVa is subjected to treatment with sodium hydroxide and then cyclized using hydrochloric acid to obtain tavaborole.

In one embodiment, in the present invention, the compound of formula IV is not isolated.

In one embodiment, in the present invention, the compound of formula IVa is not isolated.

In one embodiment, in the present invention, the compound of formula III is converted to tavaborole without isolating the compound of formula IVa.

In one embodiment, the compound of formula IV obtained after step (b) is
(1) Optionally treated with water to obtain a reaction mixture; and
(2) the reaction mixture is added to a solution of base, followed by step (c) to obtain tavaborole wherein the level of the compound of formula V is less than 0.15% w/w and/or level of the compound of formula XIV is less than 5% w/w.

In one embodiment, the present invention provides a process wherein the level of the compound of formula V and/or the level of compound of formula XIV is reduced to an extent from 20% to about 1% when determined by HPLC.

In one embodiment, the present invention provides a process for purification of tavaborole comprising isolating tavaborole from a single or mixture of organic solvent.

In one embodiment, the organic solvent may be selected from the group consisting of $C_{1-4}$ alcohols, ethers, amides, esters, nitriles, sulfoxides, ketones, hydrocarbons and halogenated hydrocarbons or mixtures thereof.

In one embodiment, the present invention provides a process for the preparation of tavaborole, a compound of formula I, comprising:

a) reacting 2-bromo-5-fluorotoluene, a compound of formula IIa

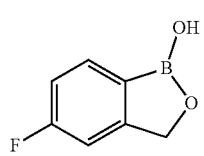

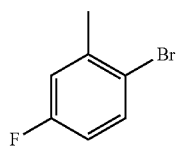

with a borate ester to obtain 2-methyl-4-fluorophenylboronic acid, a compound of formula III;

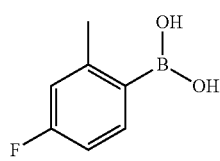

b) converting the compound of formula III to 2-bromomethyl-4-fluorophenylboronic acid, a compound of formula IVa

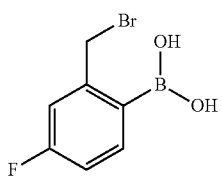

in the presence of mixture of brominating agents; and
c) cyclizing the compound of formula IV to obtain tavaborole.

In one embodiment, the steps a), b) and c) are performed as discussed supra.

In one embodiment, the present invention provides a process for the purification of tavaborole comprising isolating tavaborole from a mixture of ester and a hydrocarbon solvent.

In one embodiment, the present invention provides a process for the purification of tavaborole comprising isolating tavaborole from a mixture of ethyl acetate and heptane solvent.

In one embodiment, the present invention provides a process for the preparation of tavaborole comprising isolating tavaborole from a mixture of water and organic solvent selected from the group consisting of $C_{1-4}$ alcohols, ethers, amides, esters, nitriles, sulfoxides, ketones, hydrocarbons and halogenated hydrocarbons.

In one embodiment, the present invention provides a process for the preparation of tavaborole comprising isolating tavaborole from a mixture of water and organic solvent selected from the group consisting of $C_{1-4}$ alcohols such as methanol, ethanol, propanol, isopropanol, butanol and the like, ethers such as diethyl ether, diisopropyl ether, 1,4-dioxane, tetrahydrofuran, tetrahydropyran and the like; amides such as dimethyl acetamide, dimethylformamide and the like; esters such as ethyl acetate, butyl acetate, isopropyl acetate and the like; nitriles such as acetonitrile, propiononitrile and the like; sulfoxides such as dimethyl sulfoxides, ketones such as acetone, methyl ethyl ketone, methyl isobutyl ketone and the like; hydrocarbons such as toluene, hexane, heptane, xylene, cyclohexane and the like; and halogenated hydrocarbons such as methylene dichloride, ethylene dichloride, chloroform and the like.

In one embodiment, tavaborole, the compound of formula I may be isolated by a process comprising:
a) dissolving tavaborole in a solvent selected from the group consisting of $C_{1-4}$ alcohols, ethers, amides, esters, nitriles, sulfoxides, ketones, hydrocarbons and halogenated hydrocarbons or mixtures thereof to obtain a solution;
b) adding water as an anti-solvent to the above solution; and
c) isolating tavaborole from the above step 'b'.

In one embodiment, the solvent may be selected from the group consisting of esters such as ethyl acetate, isopropyl acetate; $C_{1-4}$ alcohols such as methanol, ethanol, propanol, isopropanol, n-butanol.

In one embodiment, the anti-solvent may be selected from the group consisting of water, hydrocarbons such as hexane, cyclohexane, heptane, toluene and xylene.

In one embodiment, in step a) of the above process, tavaborole is dissolved in solvent at a temperature in the range of about 0° C. to about reflux temp of the solvent. Preferably, the dissolution is achieved at about 40° C.

In on embodiment, the dissolution is achieved at 25-30° C.

In one embodiment, the solvent is ethanol.

In one embodiment, in step a) tavaborole is dissolved in ethanol.

In one embodiment, in step b) of the above process, to the above solution containing tavaborole in ethanol an anti-solvent was added.

In one embodiment, the addition of anti-solvent is carried out at an elevated temperature.

In one embodiment, the anti-solvent was added at 25-30° C.

In one embodiment, the anti-solvent is water.

In one embodiment, tavaborole is isolated from a mixture of $C_{1-4}$ alcohol and water.

In one embodiment, tavaborole is isolated from a mixture of ethanol and water.

In one embodiment, the present invention provides a process wherein the level of compound of formula V

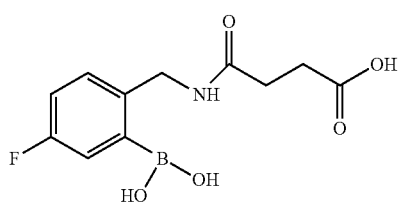

is less than 0.1% w/w with respect to the obtained tavaborole, as determined by HPLC.

In one embodiment, the present invention provides a process wherein the level of compound of formula XIV

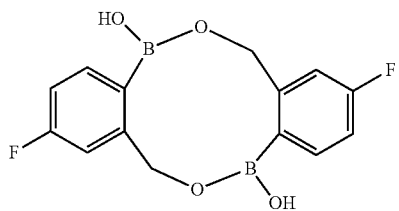

is less than 0.1% w/w with respect to the obtained tavaborole as determined by HPLC.

In one embodiment, the present invention provides amorphous tavaborole.

In one embodiment, the present invention provides crystalline tavaborole.

In one embodiment, the present invention provides crystalline tavaborole wherein the level of compound of formula V is less than 0.15% w/w with respect to the obtained tavaborole, as determined by HPLC.

In one embodiment, the present invention provides crystalline tavaborole wherein the level of compound of formula V is less than 0.1% w/w with respect to tavaborole, as determined by HPLC.

In one embodiment, the present invention provides crystalline tavaborole wherein the level of compound of formula XIV is less than 0.15% w/w with respect to the obtained tavaborole, as determined by HPLC.

In one embodiment, the present invention provides crystalline tavaborole wherein the level of compound of formula XIV is less than 0.1% w/w with respect to tavaborole, as determined by HPLC.

In one embodiment, the present invention provides crystalline tavaborole wherein the compound of formula V or the compound of formula XIV is not detected.

In one embodiment, the present invention provides a process for isolation of tavaborole, the compound of formula I, from a mixture of $C_{1-4}$ alcohol and water solvent

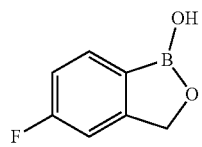

wherein, the level of the compound of formula V and/or the level of compound of formula XIV, is less than 0.5% w/w, as determined by HPLC.

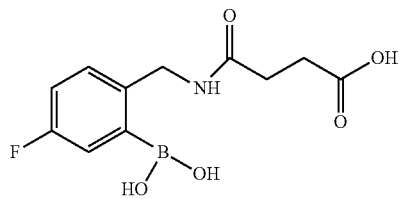

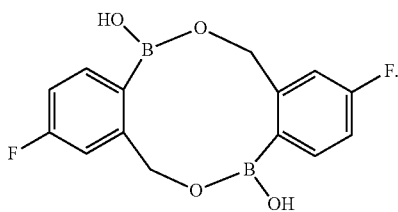

In one embodiment, the present invention provides, a process for the preparation of tavaborole, a compound of formula I, comprising:

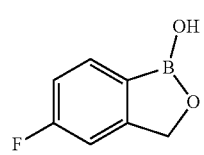

a) reacting 2-halo-5-fluorotoluene, a compound of formula II

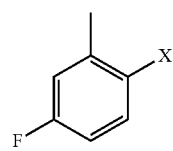

with a borate ester to obtain 2-methyl-4-fluorophenylboronic acid, a compound of formula III, wherein X is a halogen selected from chloro, bromo or iodo;

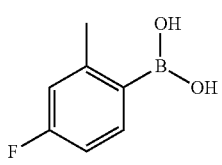

b) converting the compound of formula III to 2-halomethyl-4-fluorophenylboronic acid, a compound of formula IV

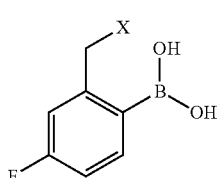

in the presence of mixture of halogenating agents;
c) cyclizing the compound of formula IV; and
d) isolating tavaborole from a mixture of $C_{1-4}$ alcohol and water solvent wherein the level of the compound of formula V and/or the level of compound of formula XIV

V

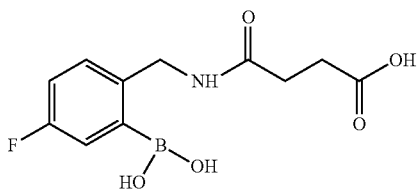

XIV

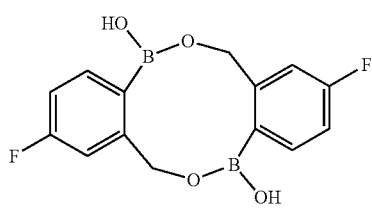

is less than 0.5% w/w with respect to the obtained tavaborole as determined by HPLC.

In one embodiment, the present invention provides a process for isolation of tavaborole the compound of formula I from a mixture of ethanol and water solvent wherein, the level of the compound of formula V and/or the level of compound of formula XIV, is less than 0.5% w/w as determined by HPLC.

In one embodiment, the present invention provides tavaborole wherein tavaborole is free of any of the below impurities:

VI

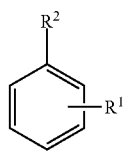

VII

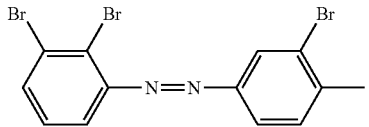

VIII

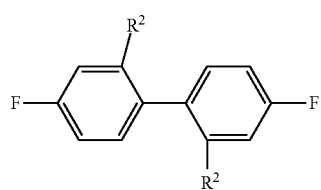

IX

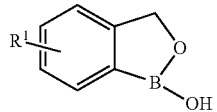

X

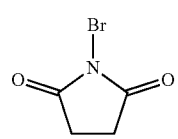

wherein $R^1$ is substituted at one or more position and may be H, amino, hydroxy, $B(OH)_2$, halo, —CHO, COOH, $CH_2OH$ $NO_2$; $R^2$ is halo or alkyl optionally substituted with one or more chloro, bromo or iodo; $R^3$ is —COOH, $B(OH)_2$; with the proviso that in compound of formula IX, $R^1$ is not fluoro at position 5.

In one embodiment, the present invention provides tavaborole wherein the level of any of the below listed impurity is less than 0.15% w/w:

XI

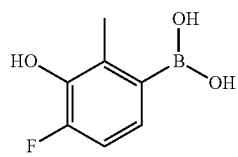

XII

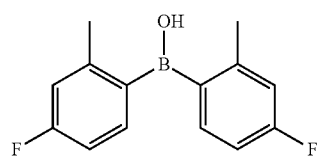

XIII

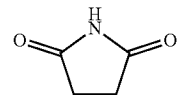

IVa

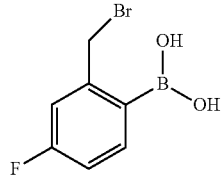

In one embodiment, the present invention provides tavaborole wherein the tavaborole is free of any of the below listed impurity:

XI

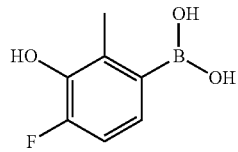

XII

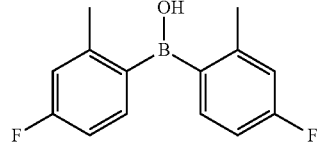

XIII

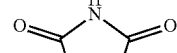

IVa

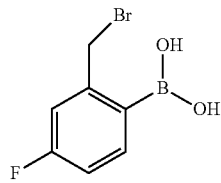

In one embodiment, the present invention provides crystalline tavaborole characterized by X-ray powder diffraction pattern which is substantially in accordance with FIG. 1.

In one embodiment, the present invention provides the compound of formula V and/or the compound of formula XIV and its use as a reference marker for the assessment of the quality of tavaborole.

In one embodiment, the present invention provides a method for preparing tavaborole, comprising the steps of:
(a) providing a batch of tavaborole or a salt thereof;
(b) assessing the purity of said batch of tavaborole, by using the compound of formula V or the compound of formula XIV as a reference marker to determine the level of compound of formula V or the compound of formula XIV

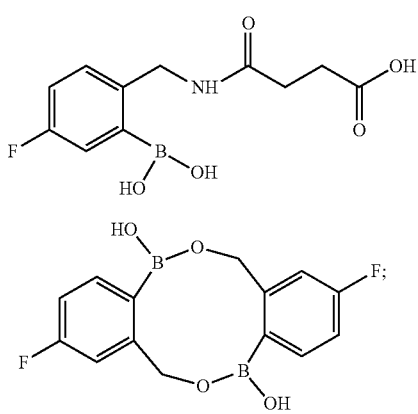

and
(c) selecting the batch of tavaborole only if the % of the compound of formula V or the compound of formula XIV is less than 0.15% w/w as determined by HPLC.

In one embodiment, the present invention provides a method for preparing tavaborole, comprising the steps of:
(a) providing a standard solution of compound of formula V or the compound of formula XIV

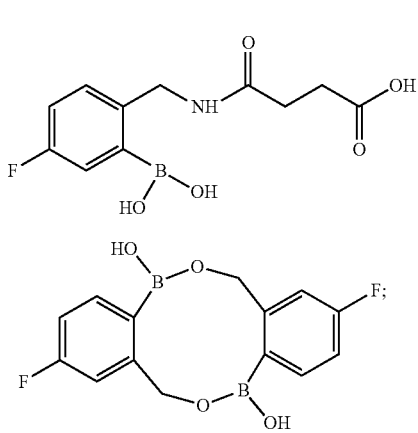

and
(b) using the solution as a reference marker to determine the level of the compound of formula V or the compound of formula XIV.

The term "reference marker", as used herein, refers to a compound that may be used in qualitative analysis to identify components of a mixture based on their position, and/or in quantitative analysis to determine the concentration of said compound in a mixture by reference to the concentration of a solution comprising a known amount of said component.

In one embodiment, according to the present invention, a reference marker solution will comprise the compound of formula V and/or the compound of formula XIV dissolved in an appropriate solvent. The method of analysis will be known to a person skilled in the art. Thus, assessing the purity of tavaborole, by using the compound of formula V and/or compound of formula XIV as reference marker, according to step (b), means determining the concentration of the compound of formula V and/or compound of formula XIV, respectively. Preferably, the concentration of the compound of formula V and/or compound of formula XIV is determined by means of conventional methods known in the art for quantifying compounds, such as HPLC.

In one embodiment, the present invention provides pharmaceutical compositions comprising tavaborole or salt thereof obtained by the processes herein described, having a $D_{50}$ and $D_{90}$ particle size of less than about 150 microns, preferably less than about 100 microns, more preferably less than about 50 microns, still more preferably less than about 20 microns, still more preferably less than about 15 microns and most preferably less than about 10 microns.

In one embodiment, the present invention provides tavaborole obtained by the processes herein described having $D_{90}$ particle size of less than about 16 microns and $D_{50}$ particle size of less than about 8 microns.

The particle size disclosed here can be obtained by, for example, any milling, grinding, micronizing or other particle size reduction method known in the art to bring the solid state tavaborole into any of the foregoing desired particle size range.

In one embodiment, the present invention provides process for preparing tavaborole, as depicted in scheme below:

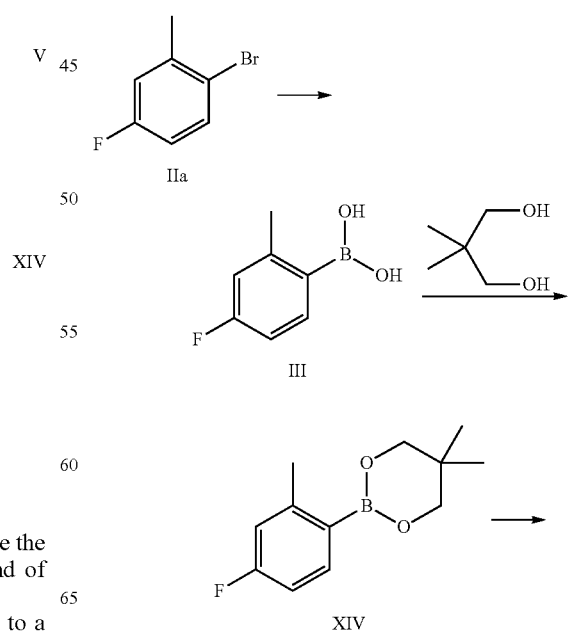

-continued

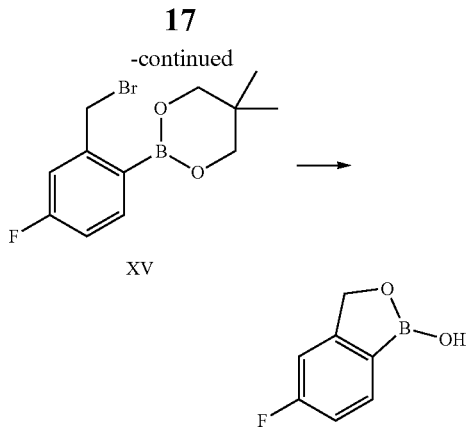

The present invention provides tavaborole as characterized and analyzed by following techniques:
HPLC method: High performance liquid chromatography (HPLC) was performed with the conditions described below for detecting purity:
Column Eclipse plus C8, 150×4.6 mm, 3.5μ, Column temperature: 40° C., Mobile phase: A=Buffer, B=Acetonitrile: Methanol:Tetrahydrofuran (50:50:03, v/v/v), Diluent: Buffer:Acetonitrile (80:20, v/v); Flow Rate: 1.0 mL/minute. Detection wavelength: UV 220 nm, Injection volume: 20 μL, Buffer: 0.01% Perchloric acid in water.
X-ray powder diffraction profile was obtained using an X-ray Diffractometer (Philips X'Pert Pro, PANalytical). The measurements were carried out with a Pre FIX module programmable divergence slit and anti-scatter Slit (Offset 0.00°); target, Cu; filter, Ni; detector, X'Celerator [1]; Scanning Mode; Active length (2Theta)=2.122°; generator 45 KV; tube current 40 mAmp. The samples were scanned in the full 20 range of 2-50° with a "time-per-step" 50 seconds.
Instrumental settings for NMR: Proton NMR spectra were recorded in DMSO-$d_6$ using NMR instrument-Varian 300 MHZ.
PSD: PSD analysis performed on Malvern Mastersizer 2000 with Sample handling unit 'Hydro2000S (A) using 0.5% w/v solution of tween 80 in water.
The examples that follow are provided to enable one skilled in the art to practice the invention and are merely illustrative of the invention. The examples should not be read as limiting the scope of the invention as defined in the features and advantages.

EXAMPLES

Example 1: Synthesis of 2-methyl-4-fluorophenylboronic acid

In a solution of 2-bromo-5-fluorotoluene (250 g) in tetrahydrofuran (250 ml) and n-hexane (250 ml) was added n-butyl lithium (991.5 ml) drop wise at −78° C. in a dry-ice bath. The solution was stirred for an hour. Triisopropyl borate (373.11 g) was added drop wise and reaction was stirred for further an hour. The resulting solution was diluted with aqueous sodium hydroxide and then washed with n-heptane. The pH of the aqueous layer was adjusted to pH 2-3 using hydrochloric acid and then extracted with ethyl acetate. The organic layer was concentrated under vacuum. This was dissolved in ethyl acetate at about 40° C. and to this heptane was added to obtain 2-methyl-4-fluorophenylboronic acid. Yield: 61.5%; HPLC purity: 99.00%.

Example 2: Synthesis of 2-methyl-4-fluorophenylboronic acid

To a solution of 1-bromo-4-fluoro-2-methylbenzene (20 g) in THF (120 ml) was added n-butyl lithium (85.9 ml) drop wise at −78° C. in a dry-ice bath, the solution was stirred for 1 h, trimethoxy borane (43.9 g) was added drop wise and reaction was stirred for further 2 h. The resulting solution was diluted with aqueous sodium hydroxide and aqueous layer was washed with n-heptane, and then pH adjusted to 2-3 with HCl (6N) and extracted with ethyl acetate and the organic layers were combined and concentrated in vacuum to give 7.5 g of 4-fluoro-2-methylphenyl boronic acid. yield: 46%, HPLC purity: 92.18%.

Example 3: Synthesis of 2-methyl-4-fluorophenylboronic acid

To dry magnesium (1.0 g) in tetrahydrofuran (20 ml) was added small amount 1,2-dibromo ethane (2 drops) and iodine. 1-bromo-4-fluoro-2methyl-benzene (2.0 g) was added to the resulting solution and refluxed for 4 h. The solution was cooled to 25-30° C. and transferred to a solution of triisopropyl borate (2.6 ml) at −78° C. The solution was warmed to 25-30° C. and stirred for 4 h. To this water was added and the mixture was concentrated followed by treatment with 2N HCl and stirred for 1 h. The suspension was extracted with diisopropyl ether and dried over sodium sulfate, filtered and concentrated, to obtain 2-methyl-4-fluorophenylboronic acid.

Example 4: Synthesis of 2-methyl-4-fluorophenylboronic acid

To dry magnesium (0.38 g) in 20 ml 2-methyl-tetrahydrofuran was added small amount of 1,2-dibromo ethane (0.97 g) and iodine. 1-bromo-4-fluoro-2-methyl-benzene (2.0 g) was added to the resulting solution and this was refluxed for 4 h. The resulting solution was cooled to 25-30° C. and transferred to a solution of triisopropyl borate (2.38 g) at −78° C. The solution was warmed to 25-30° C. and stirred for 2 h. To this water was added and the mixture was concentrated followed by treatment with 2N HCl. The reaction mixture was stirred for 1 h and then extracted with diisopropyl ether. The suspension was extracted with diisopropyl ether and dried over sodium sulfate. This was filtered and concentrated to obtain 2-methyl-4-fluorophenylboronic acid.

Example 5: Synthesis of 5-Fluoro-1,3-dihydro-1-hydroxy-2,1-benzoxaborole(tavaborole)

N-bromosuccinimide (144.51 g), AIBN (31.99 g), and catalytic quantity of bromine (2.07 g) was added to a slurry of 2-methyl-4-fluorophenylboronic acid (100.0 g) in methylene dichloride (5000.0 ml) at 34 to 37° C. The resulting reaction mixture was heated to reflux for 6 hrs. The reaction mass was washed with water at 33 to 37° C. The methylene chloride layer was added to a solution of sodium hydroxide (150.0 gm sodium hydroxide into 1500.0 ml water) at 10 to 20° C. and the methylene chloride layer was separated. The pH of aqueous layer was adjusted to pH 2-3 with conc.HCl. Compound of formula V: not detected, Compound of formula XIV: 0.9%, purity (HPLC): 98.9%.

The solid was filtered and dried in oven at 45 to 50° C. for 12 h. The crude compound was dissolved in ethyl acetate (450.0 ml) and to this was added charcoal and stirred at 40°

C. for 1 h. The reaction mass was filtered and concentrated under vacuum. The solid was dissolved in ethanol and to this water (2.5:6.0) was added. The product obtain 5-Fluoro-1,3-dihydro-1-hydroxy-2,1-benzoxaborole was filtered. Purity (HPLC): 99.9%, Compound of formula XIV: Not detected by HPLC.

$^1$H NMR (300 MHz, DMSO-d6): δ 4.97, 7.13-7.19, 7.23-7.26, 7.73-7.77, 9.24. XRD of tavaborole

| Pos. [°2Th.] | d-spacing [Å] | Rel. Int. [%] | Pos. [°2Th.] | d-spacing [Å] | Rel. Int. [%] |
|---|---|---|---|---|---|
| 5.72 | 15.44 | 0.14 | 24.35 | 3.65 | 0.89 |
| 6.37 | 13.86 | 86.48 | 24.95 | 3.56 | 2.49 |
| 12.72 | 6.95 | 41.63 | 25.45 | 3.49 | 25.59 |
| 14.39 | 6.15 | 100 | 25.56 | 3.48 | 32.13 |
| 14.95 | 5.92 | 14.09 | 26.38 | 3.37 | 5.6 |
| 16.47 | 5.38 | 47.72 | 26.97 | 3.30 | 5.13 |
| 19.10 | 4.64 | 0.23 | 27.11 | 3.28 | 8.83 |
| 20.43 | 4.34 | 14.17 | 27.96 | 3.19 | 0.97 |
| 22.41 | 3.96 | 0.35 | 28.98 | 3.08 | 11.19 |
| 23.62 | 3.76 | 0.12 | 30.12 | 2.96 | 1.3 |

Example 6: Synthesis of 5-Fluoro-1,3-dihydro-1-hydroxy-2,1-benzoxaborole Using without Mixture of Brominating Agent a) 2-methyl-4-fluorophenylboronic acid (10.0 g) was dissolved in methylene dichloride (250.00 ml). To this was added N-bromosuccinimide (13.86 g), AIBN (3.1 g), and the resulting reaction mixture was heated at reflux for 24 h. The solution was allowed to cool to 25-30° C. and to the reaction mass 20% aq sodium hydroxide was added. The pH of aqueous layer was adjusted to 2-3 with 6 N hydrochloric acid and the solid obtained was filtered. Yield: 0.25%

Example 6b)

The above example was repeated in ethyl acetate as solvent in place of methylene dichloride. yield: 0.18%

Example 6c)

The above example was repeated in chloroform as solvent in place of methylene dichloride. yield: 0.45%

Example 6d)

The above example was repeated in acetonitrile as solvent in place of methylene dichloride. yield: 0.2%

Example 6e)

The above example was repeated in chlorobenzene as solvent in place of methylene dichloride. yield: 8.8%

Example 6f)

The above example was repeated in mixture of chloroform and methylene dichloride as solvent in place of methylene dichloride. yield: 3.4%

Example 6g)

The above example was repeated using 1, 3-dibromo-5, 5-dimethylhydantoin in place of N-bromosuccinimide. yield: 0.2%

Example 6h)

The above example 6g) was repeated using bromine in carbon tetrachloride in place of methylene dichloride. yield: 0.15%

Example 7: Purification of 5-Fluoro-1,3-dihydro-1-hydroxy-2,1-benzoxaborole

5-Fluoro-1,3-dihydro-1-hydroxy-2,1-benzoxaborole (102.0 g) was dissolved in ethanol (204.0 ml). To this solution, water (1224.0 ml) was added at a temperature of about 20-30° C. The slurry was cooled, and stirred for 1 h. The solid was filtered. The product was dried in oven at 50-55° C. for 12 h. yield: 92%. HPLC purity: 100%. Compound V: Not detected, compound XIV: not detected.

Example 7a)

The above step was repeated in the same manner using methanol and water. HPLC purity: 99.29%.

Example 7b)

The above step was repeated in the same manner using isopropanol and water.

Example 7c)

The above step was repeated in the same manner using acetone and water HPLC purity: 99.91%

Example 7d)

The above step was repeated in the same manner using diisopropyl ether and heptane. HPLC purity: 99.91%

Example 7e)

Purification of 5-Fluoro-1,3-dihydro-1-hydroxy-2,1-benzoxaborole 5-Fluoro-1, 3-dihydro-1-hydroxy-2,1-benzoxaborole (60.0 g) was dissolved in toluene (300.0 ml) at 70° C. The solution was cooled to 0° C. and stirred for 1 h. The solid was filtered and dried the product in oven at 50° C. for 12 h, yield: 75%; HPLC: 99.9%.

Example 8: Process for the preparation of 3-({[2-(dihydroxyboranyl)-5-fluorophenyl] methyl} carbamoyl) propanoic acid [Compound V]

N-bromosuccinimide (13.86 g), AIBN (1.04 g), and catalytic quantity of bromine (2.07 g) was added to a slurry of 2-methyl-4-fluorophenylboronic acid (10.0 g) in chloroform (50.0 ml) at 25° C. The resulting reaction mixture was heated at 65 to 70° C. for 6 hrs. Aqueous sodium hydroxide solution (20%) was added into the reaction mass at 0 to 10° C. The organic layer was separated and pH of aqueous layer was adjusted to 2-3 with conc. hydrochloric acid. The solid was filtered and dried in oven at 45 to 50° C. for 12 h. The title compound was purified by column chromatography. $^1$H NMR (DMSO): δ 2.414-2.497, 3.335, 4.387-4.408, 6.999-7.030, 7.540, 8.315, 8.470, 12.094.

Example 9: Process for the Preparation of 7,16-difluoro-3,12-dioxa-2,11 diboratricyclo[12.4.0.0$^{5,10}$] octadecal(14),5,7,9,15,17-hexaene-2,11-diol Compound XIV)

Sodium bicarbonate (10.0 g) was added to the reaction mass of 2-Bromo-methyl-4-fluoro-phenylboronic acid in mixture of ethanol (100.0 ml) and water (150.0 ml) at 25° C. The resulting reaction mixture was stirred at 25° C. for 15 hrs. The pH of reaction mass was adjusted to 2-3 with aq. hydrochloric acid. The product obtained was filtered. $^1$H NMR (DMSO): δ 2.502, 3.337, 4.728, 7.061-7.088, 7.200-7.230, 7.547-7.595, 8.059.

We claim:

1. A process for the preparation of tavaborole, a compound of formula I, comprising:

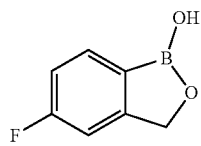
I a) reacting 2-halo-5-fluorotoluene, a compound of formula II

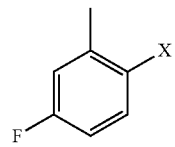
II with a borate ester to obtain 2-methyl-4-fluorophenylboronic acid, a compound of formula III, wherein X is a halogen selected from chloro, bromo or iodo;

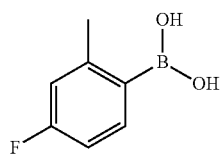
III b) converting the compound of formula III to 2-halomethyl-4-fluorophenylboronic acid, a compound of formula IV

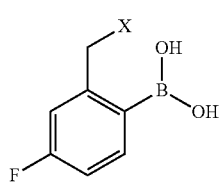
IV in the presence of mixture of halogenating agents; and
c) cyclizing the compound of formula IV to obtain tavaborole.

2. The process as claimed in claim 1, wherein in step b) the mixture of halogenating agents is a mixture of brominating agents.

3. The process as claimed in claim 2, wherein in step b) the mixture of brominating agents comprises bromine and N-bromosucciminide.

4. The process as claimed in claim 3, wherein bromine is used in catalytic amount to the amount of N-bromosuccinimide.

5. The process as claimed in claim 1, wherein in step b) halogenation is carried out in the presence of a radical initiator.

6. The process as claimed in claim 1, further comprising isolating tavaborole from a mixture of water and an organic solvent selected from the group consisting of $C_{1-4}$ alcohols, ethers, amides, esters, nitriles, sulfoxides, ketones, hydrocarbons and halogenated hydrocarbons and mixtures thereof.

7. The process as claimed in claim 6, wherein the isolating comprises:

a) dissolving tavaborole in a solvent selected from the group consisting of $C_{1-4}$ alcohols, ethers, amides, esters, nitriles, sulfoxides, ketones, hydrocarbons and halogenated hydrocarbons and mixtures thereof to obtain a solution;

b) adding water as an anti-solvent to the above solution; and c) isolating tavaborole from the above step (b).

8. The process as claimed in claim 6, wherein the isolation comprises isolating from a mixture of $C_{1-4}$ alcohol and water solvent.

9. The process as claimed in claim 8, wherein a level of the compound of formula V and/or the level of compound of formula XIV

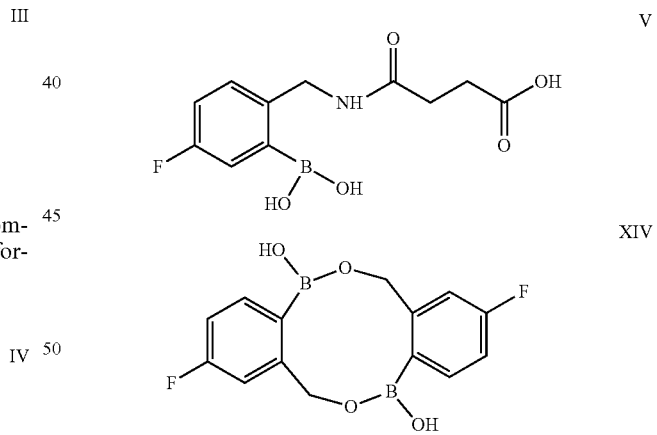

is less than 0.5% w/w with respect to the obtained tavaborole as determined by HPLC.

10. A method for preparing tavaborole, comprising the steps of:

(a) providing a batch of tavaborole or a salt thereof thereof prepared by the process as claimed in claim 1;

(b) assessing the purity of said batch of tavaborole, by using a compound of formula V or a compound of formula XIV as a reference marker to determine the level of the compound of formula V or the compound of formula XIV

V

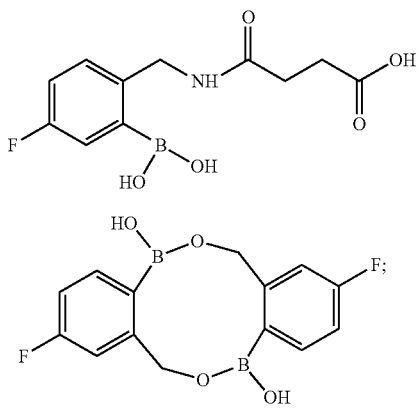

XIV and
(c) selecting the batch of tavaborole only if the % of the compound of formula V or the % of the compound of formula XIV is less than 0.15% w/w as determined by HPLC.

11. A method for preparing tavaborole thereof as prepared by the process as claimed in claim 1, further comprising the steps of:

(a) providing a standard solution of compound V or compound XIV

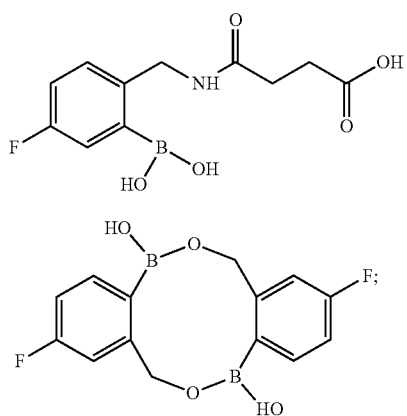

(b) using the standard solution as a reference marker to determine a level of the compound of formula V or the compound of formula XIV in tavaborole.

\* \* \* \* \*